US009962628B2

United States Patent
Sheriff et al.

(10) Patent No.: US 9,962,628 B2
(45) Date of Patent: May 8, 2018

(54) USE OF CITRATE SOLUTION FOR AFFINITY CHROMATOGRAPHIC PURIFICATION OF CRP USING PHOSPHOCHOLINE AND DERIVATIVES THEREOF

(71) Applicant: Pentracor GmbH, Hennigsdorf (DE)

(72) Inventors: Ahmed Sheriff, Berlin (DE); Birgit Vogt, Berlin (DE); Stephan Mattecka, Berlin (DE)

(73) Assignee: Pentracor GmbH, Hennigsdorf (DE)

( * ) Notice: Subject to any disclaimer, the term of this patent is extended or adjusted under 35 U.S.C. 154(b) by 0 days. days.

(21) Appl. No.: 15/526,263

(22) PCT Filed: Nov. 12, 2015

(86) PCT No.: PCT/EP2015/076493
§ 371 (c)(1),
(2) Date: May 11, 2017

(87) PCT Pub. No.: WO2016/075269
PCT Pub. Date: May 19, 2016

(65) Prior Publication Data
US 2017/0319982 A1 Nov. 9, 2017

(30) Foreign Application Priority Data
Nov. 12, 2014 (EP) .................................. 14192831

(51) Int. Cl.
*B01D 15/38* (2006.01)
*B01D 15/12* (2006.01)
(Continued)

(52) U.S. Cl.
CPC ......... *B01D 15/3804* (2013.01); *B01D 15/12* (2013.01); *B01J 20/3242* (2013.01);
(Continued)

(58) Field of Classification Search
CPC .... B01D 15/38; B01D 15/3804; B01D 15/12; B01D 15/16; B01D 15/20; B01D 15/206;
(Continued)

(56) References Cited

U.S. PATENT DOCUMENTS 5,283,238 A * 2/1994 Potempa ................ A61K 9/127
424/499
2007/0225226 A1 9/2007 Hammond et al.
(Continued)

FOREIGN PATENT DOCUMENTS

JP      S62-36399      2/1987
WO    WO 90/12632    11/1990
(Continued)

OTHER PUBLICATIONS

Nilsson et al. Comparison of soluble thrombomodulin, von Willebrand factor, tPA/PAI-1 complex, and high-sensitivity CRP concentrations in serum, EDTA plasma, citrated plasma, and acidified citrated plasma (Stabilyte(TM)) stored at −70C for 8-11 years. Thrombosis Research (2005) 116, 249-254. (Year: 2005).*
(Continued)

*Primary Examiner* — Katherine Zalasky
(74) *Attorney, Agent, or Firm* — Knobbe, Martens, Olson & Bear, LLP

(57) ABSTRACT

The invention relates to the use of a citrate solution for affinity-chromatographic removal of C-reactive protein (CRP) from biological fluids, wherein the CRP is affinity-chromatographically removed using ($Ca^{2+}$-dependent) binding of CRP to a column material functionalized with ω-phosphonooxyalkyl ammonium groups and/or with ω-ammoniumalkoxy-hydroxy-phosphoryloxy groups.

11 Claims, 2 Drawing Sheets

(51) Int. Cl.
B01J 20/286 (2006.01)
B01J 20/32 (2006.01)
C07K 14/47 (2006.01)
B01J 20/22 (2006.01)
B01J 20/281 (2006.01)
B01J 20/285 (2006.01)

(52) U.S. Cl.
CPC ....... B01J 20/3255 (2013.01); C07K 14/4737 (2013.01); *B01J 20/22* (2013.01); *B01J 20/285* (2013.01); *G01N 30/48* (2013.01)

(58) Field of Classification Search
CPC .. B01D 15/424; B01D 15/426; B01D 15/422; G01N 30/48; G01N 30/482; G01N 30/02; G01N 2030/484; B01J 20/283; B01J 20/288; B01J 20/289; B01J 20/286; B01J 20/3231; B01J 20/3242; B01J 20/3244; B01J 20/3246; B01J 20/3248; B01J 20/3251; B01J 20/3255; B01J 20/285; B01J 20/291; B01J 20/22; B01J 20/24

See application file for complete search history.

(56) References Cited

U.S. PATENT DOCUMENTS

| | | | |
|---|---|---|---|
| 2009/0196937 A1 | 8/2009 | Vogt | |
| 2009/0196938 A1* | 8/2009 | Vogt | A61M 1/3633 424/530 |
| 2010/0098686 A1* | 4/2010 | Bhardwaj | C07K 16/18 514/1.1 |

FOREIGN PATENT DOCUMENTS

| | | |
|---|---|---|
| WO | WO 2004/076486 | 11/2004 |
| WO | WO 2007/076844 | 7/2007 |

OTHER PUBLICATIONS

Osmand et al. Interactions of C-reactive protein with the complement system. The Journal of Experimental Medicine (1975) 142, 1065-1077. (Year: 1975).*
Black et al., "Minireviews: C-reactive Protein," The Journal of Biological Chemistry, dated Aug. 26, 2004, vol. 279, pp. 48487-48490.
Nunomura, W. et al., "Purification of Human C-reactive Protein by Immunoaffinity Chromatography using Mouse Monoclonal Antibody," Journal of Biochemical and Biophysical Methods, dated Feb. 12, 1990, vol. 21, pp. 75-80.
Nurmohamed et al., "Reverse Epidemiology: Paradoxical Observations in Haemodialysis Patients," The Journal of Medicine, dated Nov. 2005, vol. 63, No. 10, pp. 376-381.
Pepys et al., "C-reactive Protein: a Critical Update," Journal of Clinical Investigation, 2003, vol. 111, pp. 1805-1812.
Slagman et al., "Specific Removal of C-Reactive Protein by Apheresis in a Porcine Cardiac Infarction Model," Blood Purification, dated Dec. 7, 2010, vol. 31, pp. 9-17.
Sola et al., "Statin Therapy is Associated with Improved Cardiovascular Outcomes and Levels of Inflammatory Markers in Patients with Heart Failure," Journal of Cardiac Failure, 2005, vol. 11, No. 8, pp. 607-612.
Thompson et al., "The Physiological Structure of Human C-reactive Protein and its Complex with Phosphocholine," Structure, Feb. 1999, vol. 7, pp. 169-177.
Tseng J. et al., "Binding of Human C-reactive Protein (CRP) to Plasma Fibronectin Occurs via the Phosphorylcholine-Binding site," Molecular Immunology, 1988, vol. 25, No. 8, pp. 679-686.
Yeh, "High-Sensitivity C-reactive Protein as a Risk Assessment Tool for Cardiovascular Disease," Clinical Cardiology, 2005, vol. 28, pp. 408-412.
Zoccali et al., "Predictors of Cardiovascular Death in ESRD," Seminars in Nephrology, 2005, vol. 25, pp. 358-362.

* cited by examiner

Comparison of the depletion performance with (ACD-A) and without (control) citrate

USE OF CITRATE SOLUTION FOR AFFINITY CHROMATOGRAPHIC PURIFICATION OF CRP USING PHOSPHOCHOLINE AND DERIVATIVES THEREOF

The present invention relates to the use of a citrate solution for the affinity-chromatographic removal of C-reactive protein (CRP) from biological fluids, wherein the affinity-chromatographic removal of CRP is performed by (a $Ca^{2+}$-dependent) binding of CRP to a column material functionalized with ω-phosphonooxyalkyl ammonium groups and/or with ω-ammoniumalkoxy-hydroxy-phosphoryloxy groups.

BACKGROUND OF THE INVENTION

According to the World Health Organization (WHO), around 17,000,000 people died of cardiovascular diseases in 2008. Thus, cardiovascular diseases are the most frequent cause of death among non-infectious diseases and are responsible for approximately one-third of all deaths worldwide. According to estimates, this number will rise to about 23,000,000 deaths per year by 2030.

Thus, cardiovascular diseases are not only the main cause of death worldwide but also cause enormous medical costs for national health systems and health insurance funds. Two of the most common and most damaging manifestations of cardiovascular disease are the occurrence of arteriosclerosis and thrombosis, which in return are, among other, responsible for heart attacks and strokes.

In recent years, major advances have been made in the treatment of cardiovascular diseases. This progress has been made possible not only by growing insights regarding the disease-inducing mechanisms, but also by the early identification of risk patients. In fact, the identification of disease risks and their early treatment are important characteristics of modern medical practice. Over the past 25 years, a variety of factors and clinical parameters have been identified that correlate either with the current condition of the disease or with the likelihood of cardiovascular disease in the future. Such risk factors can be measurable biochemical or physiological parameters such as, serum cholesterol, HDL, LDL and fibrinogen levels, but also behavioral patterns such as overweight and smoking. In cases in which a risk factor is not merely indicative of a disease or its development, but is actually causally involved in its development, a therapeutic influence on this risk factor can influence the course of the disease or reduce the risk of its development.

C-reactive protein (CRP) as an acute phase protein is part of the innate immune system and is formed in the liver in the course of inflammatory reactions and released into the blood. The formation of CRP is primarily induced by cytokines that are expressed in the context of an acute or chronic inflammatory reaction. The most powerful stimulus for the formation of CRP is the interleukin-6 (IL-6). Therefore, the levels of CRP as well as IL-6 in blood are indicators of a local or systemic inflammatory response. It is presumed that chronic inflammation is one of the underlying and supporting pathological manifestations of cardiovascular diseases. It is increasingly assumed that CRP is not only predicative for cardiovascular disease, but is also causally involved in its development or can influence its course.

Yeh (*Clin Cardiol.*, 2005, 28, 408-412) shows that the CRP level can be used to predict cardiovascular disease risk, CRP is also an indicator of inflammatory responses, and that inflammation promotes all stages of atherosclerosis. Zoccali et al., (*Semin. Nephrol.* 2005, 25, 358-362) show that the CRP level is predictive of the cardiovascular mortality risk in patients with renal disease in the terminal stage. According to Nurmohamed et al., (*Neth. J. Med.* 2005, 63, 376-381), the CRP level is predictive of cardiovascular mortality risk in hemodialysis patients.

Sola et al. (*J. Card. Fail.* 2005, 11, 607-612) have shown that statin therapies can be used to reduce the amount of CRP and thus reduce the mortality and morbidity caused by cardiovascular disease. However, this form of therapy does not significantly reduce the high CRP levels (up to 1000-fold above normal values) resulting from a myocardial infarction or the high CRP levels in the blood of dialysis patients.

The normal value for CRP in the blood of humans varies from person to person, but is in the median at approximately 0.8 mg CRP per liter of blood, but can be in the case of acute or chronic inflammatory reactions (e.g. bacterial infections, atherosclerosis, after a heart attack) to levels substantially above 100 mg CRP per liter of blood. Since the half-life of CRP in the blood (approx. 19 hours) is constant and thus independent of the health condition of the patient, the synthesis rate of CRP alone is responsible for the regulation of the CRP level in the blood (Pepys & Hirschfield, *J. Clin. Invest.* 2003, 11, 1805-1812). Therefore, the greatly increased synthesis of CRP in acute pathological conditions places particular demands on therapeutic approaches to CRP removal of patients (risk patients or acute patients) since a significant amount of CRP needs to be removed in order to lower CRP levels to standard blood levels.

Consequently, there is an increasing interest in therapeutic procedures for reducing CRP levels in patients' blood. Due to the clinical significance of CRP there is also an interest in effective methods for the purification of CRP, in order to use the purified CRP in further experiments, e.g. for the investigation of its molecular function subsequently.

WO 2004/076486 discloses a method for inhibiting immunological, inflammatory and/or pathophysiological responses by administering CRP-binding molecules to patients with an increased CRP level. However, the extracorporeal treatment of biological fluids for the removal of CRP from said biological fluids is not disclosed.

WO 90/12632 discloses a method and device for the extracorporeal treatment of biological fluids with the aim of removing CRP as well as anti-phosphocholine antibodies from these biological fluids for the treatment of cancer. The phosphocholine-containing matrix used for this purpose can consist of e.g. silica, sepharose, acrylic beads or agarose, wherein both CRP and anti-phosphocholine antibodies are bound by means of the containing phosphocholine.

US 2007/225226 A1 discloses specific peptides which bind CRP and can therefore be used as a functional column material in a CRP apheresis. This binding takes place independently of calcium. Also some extracorporeal blood purification devices employing this column material for CRP apheresis are described, including a system for removing endotoxins using citrate as an anti-coagulant. CRP is a pentamer whose subunits are each associated with two $Ca^{2+}$ ions which bind to the ligands used in this invention. Since citrate binds $Ca^{2+}$ ions with high affinity, it has so far been assumed that when $Ca^{2+}$-dependent ligands are used, citrate has a negative effect on the capacity of the columns to bind CRP. However, the inventors of the present application have shown that the capacity is higher for the used ligands. CRP is an opsonin and can activate the complement system via C1q in bound form. Surprisingly, however, it has been shown that citrate prevents the activation of the complement, which further increases the capacity so that citrate increases further the capacity of the used ligands. This effect occurring with $Ca^{2+}$-dependent ligands is also completely surprising in the light of US 2007/225226 A1.

WO 2007/076844 discloses a method by extracorporeal CRP removal from the blood plasma by means of apheresis to reduce the risk to a patient (caused by an increased CRP level in the blood). According to the invention, a matrix-containing column is used to which phosphocholine derivatives are bound to bind CRP and remove it from the plasma, thus treating and/or preventing autoimmune diseases, cardiovascular diseases, diabetes and renal insufficiency.

Slagman et al. (*Blood Purif.* 2011, 31, 9) demonstrates on the pig model the successful reduction of CRP levels in the blood by extracorporeal apheresis after a heart attack.

A problem that occurs in the extracorporeal use of blood and blood plasma, whether in analytical or preparative applications but also in dialysis or apheresis, is the beginning of blood clotting, which hinder both the use itself or makes it impossible, but it also clogs as well as contaminates the used devices. For this reason, anti-clotting agents (so-called anticoagulants) are directly added to the blood or blood plasma after removal from the human or animal body.

One possibility for inhibiting blood coagulation is the administration of $Ca^{2+}$ chelators such as EDTA (ethylenediaminetetraacetic acid), oxalate and citrates. Calcium is needed as a cofactor of some coagulation factors during blood clotting. $Ca^{2+}$ chelators are used to remove calcium from the blood or blood plasma, thus inhibiting the coagulation. However, this is a significant problem for affinity chromatographic methods for the removal of CRP by means of phosphocholine or phosphoethanolamine or phosphocholine derivatives or phosphoethanolamine derivatives. Since the binding of CRP to phosphocholine or its derivatives $Ca^{2+}$ is required (Black et al., Journal of Biological Chemistry, 2004, 279: 48487, Thompson et al., Structure 1999, 7 (2), 169-177), the unanimous opinion in the prior art was that an administration of $Ca^{2+}$ chelators during the binding of CRP to phosphocholine should be avoided absolutely (see, for example, WO 90/12632). Thus, according to the prior art, the use of citrate-containing binding buffers during the affinity-chromatographic binding of CRP to phosphocholine is completely unsuitable. However, citrate-containing solutions (similar to administration of EDTA) were suitable as elution buffers, i.e. to remove the bound CRP from phosphocholine.

One possibility for $Ca^{2+}$ independent anticoagulation consists in the administration of heparin. Heparin is a endogenous substance that is produced by mast cells and has an inhibitory effect on the coagulation cascade. By binding heparin to antithrombin II, a protease inhibitor circulating in the blood, which can inactivate activated coagulation factors such as thrombin and factor Xa, a conformational change of the antithrombin II is triggered. This accelerates the antithrombin II-mediated inactivation of coagulation factors by 2,000 times. Blood clotting comes to a standstill. Accordingly, in methods for the affinity-chromatographic removal of CRP from blood or blood plasma by means of phosphocholine and phosphocholine derivatives or phosphoethanolamine and phosphoethanolamine derivatives, heparin has hitherto exclusively been used as an anticoagulant.

However, this has some disadvantages, since heparin, especially in the case of unfractionated heparin, can lead to an immune reaction, the heparin-induced thrombocytopenia (HIT), in addition to hemorrhage. Thereby, heparin induces venous and arterial thromboses. In stroke patients in whom the use of CRP apheresis is also possible, the risk of HIT when receiving unfractionated heparin is approx. 3%. In addition, heparin is not approved for use with centrifugal cell separators which are often used to separate blood into the cellular components and the blood plasma.

It is an objective of the present invention to provide an anticoagulant for an affinity-chromatographic removal of CRP, which avoids the heparin-related problems from the state of the art and additionally does not impair the $Ca^{2+}$-dependent binding of CRP to phosphocholine or phosphoethanolamine and their derivatives.

This objective is achieved by the teachings of the independent claims. Further advantageous embodiments are evident from the description, the examples and the dependent claims.

Surprisingly, it could be found that the use of a citrate solution for affinity-chromatographic removal of CRP from biological fluids using a column material functionalized with ω-phosphonooxyalkyl ammonium groups and/or with ω-ammoniumalkoxy-hydroxy-phosphoryloxy groups not only surprisingly achieves an efficient removal of CRP from biological fluids but also solves the problems of the prior art.

DESCRIPTION OF THE INVENTION

The present invention relates to the use of a citrate solution for the affinity-chromatographic removal of CRP from biological fluids using a column material functionalized with ω-phosphonooxyalkyl ammonium groups and/or with ω-ammoniumalkoxy-hydroxy-phosphoryloxy groups.

The term "CRP" as used herein is equivalent to "C-reactive protein". Herein, it preferably refers to the human C-reactive protein.

The term "affinity-chromatographic removal of CRP" as used herein means that the removal of the CRP occurs through a specific binding between the CRP and the components of the means for removal of CRP. In this context, it is also possible to refer to an "affinity-chromatographic removal of CRP" or a "selective removal of CRP". Such a specific binding between CRP and a suitably functionalized column material is based on the structural properties of the CRP protein and may include, for example, the characteristic binding of CRP to phosphocholine or the binding of CRP to antibodies directed against an epitope of the CRP. The selective or molecular-specific removal of CRP involves that CRP binds with higher affinity to the functionalized column material than to other components of the biological fluids. The term "selective" with respect to the removal of CRP as used in the present application therefore means that the ratio of removed CRP to the amount of CRP contained in the biological fluid is at least three times as high as the respective ratio of other removed substances to the amount of the substance contained in the biological fluid. However, the term "selective" with respect to the removal of CRP as used in the present application does not mean that only CRP is removed. Here, it is obvious to the person skilled in the art that with such an affinity chromatography removal of CRP to some extent, other substances (unintentionally) can inevitably bind to the column material, and thus are also removed to a certain extent. If a structural congruence with the structure of the CRP responsible for specific binding to the ω-phosphonooxyalkyl ammonium groups and/or with ω-ammoniumalkoxy-hydroxy-phosphoryloxy groups exist such as in a protein, this structurally similar protein is also bound to a certain degree. An example could be antibodies directed against phosphocholine and therefore can also be bound to a column material which has been functionalized with phosphocholine. Another possibility is the never entirely avoidable unspecific binding of components of the biological fluid to for example matrix substrate materials.

As already mentioned, the binding of CRP to phosphocholine or its derivatives or to phosphoethanolamine or its derivatives is dependent on the presence of $Ca^{2+}$ and thus also the binding of CRP to ω-phosphonooxyalkyl ammonium groups and/or with ω-ammoniumalkoxy-hydroxy-phosphoryloxy groups which were immobilized in or on a column material is also dependent on the presence of $Ca^{2+}$.

Therefore, the present invention also relates to the use of citrate solution for affinity-chromatographic removal of CRP from biological fluids, wherein the affinity-chromatographic removal of CRP is performed by (a $Ca^{2+}$-dependent) binding of CRP to a column material functionalized with ω-phosphonooxyalkyl ammonium groups and/or with ω-ammoniumalkoxy-hydroxy-phosphoryloxy groups.

Of course, the use according to the invention of a citrate solution for affinity-chromatographic removal of CRP from biological fluids, wherein affinity-chromatographic removal of CRP is performed by (a $Ca^{2+}$-dependent) binding of CRP to a functionalized column material with ω-phosphonooxyalkyl ammonium groups and/or with ω-ammoniumalkoxy-hydroxy-phosphoryloxy groups, means that the citrate solution is mixed with the biological fluid from which the CRP should be removed prior to CRP removal. The citrate solution is thus present during the desired binding of CRP to the ω-phosphonooxyalkyl ammonium groups and/or ω-ammoniumalkoxy-hydroxy-phosphoryloxy groups of the column material. One could therefore also say according to technical terms from the field of affinity-chromatography that the citrate solution is used as "a binding buffer".

However, it does not mean that the citrate solution is used as "elution solution" (or as "elution buffer") and thus is used for the removal of CRPs from the column material functionalized with ω-phosphonooxyalkyl ammonium groups and/or ω-ammoniumalkoxy-hydroxy-phosphoryloxy groups, i.e. for the regeneration of the column material.

The term "binding buffer" (also referred to "binding solution"), as used herein, refers in case of an affinity-chromatographic method for removal of a substance (herein the selective and $Ca^{2+}$-dependent removal of CRP) from a sample (here biological fluids such as blood or blood plasma) to a solution which is added to the sample and then applied together with the sample onto the column material (here column material functionalized with ω-phosphonooxyalkyl ammonium groups and/or ω-ammoniumalkoxy-hydroxy-phosphoryloxy groups) for the removal of the substance. The binding buffer should provide adequate conditions for the specific binding of the substance to be removed to the column material.

The term "elution buffer" (also referred to as "elution solution"), as used herein, refers in case of an affinity-chromatographic method for removal of a substance (here the selective and $Ca^{2+}$-dependent removal of CRP) from a sample (here biological fluids such as blood or blood plasma) to a solution which is applied after applying the sample onto the column material and the occurred specific binding of the substance to be removed to the column material in order to break the specific binding again and thus to detach the substance to be removed from the column material (or to elute). In contrast to the binding buffer, conditions should therefore be created in the column material by the elution buffer which do not allow a binding of the substance to be removed but on the contrary prevent it.

The present invention therefore also relates to the use of a citrate solution for the affinity-chromatographic removal of CRP from biological fluids, wherein the affinity-chromatographic removal of CRP is performed by (a $Ca^{2+}$-dependent) binding of CRP to a column material functionalized with ω-phosphonooxyalkyl ammonium groups and/or with ω-ammoniumalkoxy-hydroxy-phosphoryloxy groups, wherein the citrate solution serves as a binding buffer (or binding solution) for the affinity-chromatographic removal of CRP from biological fluids.

The term "biological fluid" as used herein refers to aqueous solutions which occur in mammals and preferably humans such as cerebrospinal fluid, peritoneal fluid, pleural fluid, ascites fluid, blood, blood plasma, liver extracts and interstitial fluid. The present invention, of course, relates to biological fluids containing CRP.

The present invention is therefore also directed to the use of a citrate solution for the affinity-chromatographic removal of CRP from biological fluids by means of a column material functionalized with ω-phosphonooxyalkyl ammonium groups and/or ω-ammoniumalkoxy-hydroxy-phosphoryloxy groups, wherein the biological fluids are blood or blood plasma.

In other words, the present invention is also directed to the use of a citrate solution for the affinity-chromatographic removal of CRP from blood and/or blood plasma by means of a column material functionalized with ω-phosphonooxyalkyl ammonium groups and/or ω-ammoniumalkoxy-hydroxy-phosphoryloxy groups.

Citrate Solutions

The term "citrate" as used herein refers to the citrate anion, or the salt of citric acid, or, in other words, an organic tricarboxylate of the following chemical formula:

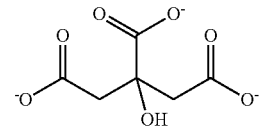

The citrate can occur in various forms (or compounds), thus e.g. as citric acid (in one- to three-fold protonated form), as a salt of citric acid in combination with others (other than $H^+$) inorganic cations (e.g. as a metal salt together with metal cations or as an ammonium salt together with ammonium ions), but also as a partial citrate ester. In this context, the term "citrate compound" is also used herein.

If the salt of citric acid, i.e. the citrate anion, is complexed with an inorganic cation, the term "citrate salt" is also referred to herein as a specific form of the citrate compound.

As used herein, the term "citrate solution" thus comprises aqueous solutions containing at least one citrate compound. More detailed information on the composition of the citrate solution is given below.

According to the invention, however, it is preferred if the citrate concentration in the citrate solution is not less than 1 mM, preferably not less than 1.1 mM, preferably not less than 1.2 mM, more preferably not less than 1.3 mM, still more preferably not less than 1.4 mM and most preferably not less than 1.5 mM.

In addition, according to the invention, it is preferred if the citrate compound(s) is an essential component of the citrate solution according to the invention. Here, "essential component" means that the sum of the molar concentrations of all citrate compounds in the citrate solution, compared to the other compounds within the citrate solution, but excluding water, is among the three highest concentrations occurred in the citrate solution.

The present invention therefore also relates to the use of a citrate solution for the affinity-chromatographic removal of CRP from biological fluids by means of a column material functionalized with ω-phosphonooxyalkyl ammonium groups and/or ω-ammoniumalkoxy-hydroxy-phosphoryloxy groups, wherein the citrate solution contains at least one of the citrate compounds from the group comprising or consisting of citric acid, sodium dihydrogen citrate, disodium hydrogen citrate, trisodium citrate, trisodium citrate dihydrate, potassium dihydrogen citrate, dipotassium hydrogen citrate, tripotassium citrate, lithium dihydrogen citrate, dilithium hydrogen citrate, trilithium citrate, ammonium dihydrogen citrate, diammonium hydrogen citrate, triammonium citrate, tricalcium dicitrate (calcium citrate), trimagnesium dicitrate (magnesium citrate) and/or partial citrate esters.

According to the present invention, it is also possible that the citrate solution contains a mixture of several of the citrate compounds listed above.

The term "citrate compound" as used herein comprises both citric acid and its salts.

If the general term "sodium citrate" is used in this application, this term encompasses the various protonated forms of the sodium citrate, i.e. the unprotonated (trisodium citrate), the single protonated (disodium hydrogen citrate) or the double protonated form (sodium dihydrogen citrate).

If the general term "potassium citrate" is used in this application, this term encompasses the various protonated forms of the potassium citrate, i.e. the unprotonated (tripotassium citrate), the single protonated (dipotassium hydrogen citrate) or the double protonated form (potassium dihydrogen citrate).

If the general term "lithium citrate" is used in this application, this term encompasses the various protonated forms of the lithium citrate, i.e. the unprotonated (trilithium citrate), the single protonated (dilithium hydrogen citrate) or the double protonated form (lithium dihydrogen citrate).

If the general term "ammonium citrate" is used in this application, this term encompasses the various protonated forms of the ammonium citrate, i.e. the unprotonated (triammonium citrate), the single protonated (diammonium hydrogen citrate) or the double protonated form (ammonium dihydrogen citrate).

The term "partial citrate ester" as used herein refers to ester of citric acid, however, not all three carboxyl groups (i.e. —COO$^-$) of the citrate are esterified (i.e. —COOR, where R is an organic residue) but at most two of the three carboxyl groups of the citrate, but preferably at most one of the three carboxyl groups of the citrate are esterified. In addition to the one or two ester groups, the partial citrate ester also contains one or two physiologically acceptable inorganic cations (e.g. metal cations, such as Na$^+$, K$^+$), which complex the one or two non-esterified carboxyl group(s) of the citrate.

A preferred embodiment of the present invention therefore relates to the use of a citrate solution for the affinity-chromatographic removal of CRP from biological fluids by means of a column material functionalized with ω-phosphonooxyalkyl ammonium groups and/or ω-ammoniumalkoxy-hydroxy-phosphoryloxy groups, wherein the citrate solution contains at least one of the citrate compounds from the group comprising or consisting of citric acid, sodium dihydrogen citrate, disodium hydrogen citrate, trisodium citrate, trisodium citrate dihydrate, potassium dihydrogen citrate, dipotassium hydrogen citrate, tripotassium citrate, lithium dihydrogen citrate, dilithium hydrogen citrate, trilithium citrate, ammonium dihydrogen citrate, diammonium hydrogen citrate, triammonium citrate, tricalcium dicitrate (calcium citrate), trimagnesium dicitrate (magnesium citrate) and/or partial citrate esters, wherein the at least one citrate compound is selected from citric acid and citrate salts with monovalent metal cations.

It is preferred according to the invention, if the citrate solution contains no iron(II) citrate. More preferably, the citrate solution does not contain iron(III) citrate. In addition, it is preferred according to the invention, if the citrate solution contains no copper(II) citrate (tricopper dicitrate) and no aluminum citrate.

In further preferred embodiments of the present invention, the citrate solution does not contain calcium citrate (also known as tricalcium dicitrate).

In a further preferred embodiment of the present invention, the citrate solution contains no magnesium citrate (also known as trimagnesium dicitrate) or magnesium citrate in a concentration of at most 1 mM.

In a further preferred embodiment of the present invention, the citrate solution contains no calcium citrate and no magnesium citrate or magnesium citrate in a concentration of at most 1 mM.

When mentioned in the present application that a solution does not contain a certain substance, this means that this solution does not contain the substance at all or at least does not contain more than 0.01% by weight of this substance to account for possible unavoidable impurities.

A particularly preferred embodiment of the present invention therefore relates to the use of a citrate solution for the affinity-chromatographic removal of CRP from biological fluids by means of a column material functionalized with ω-phosphonooxyalkyl ammonium groups and/or ω-ammoniumalkoxy-hydroxy-phosphoryloxy groups, wherein the citrate solution contains at least one of the citrate compounds from the group comprising or consisting of citric acid, sodium dihydrogen citrate, disodium hydrogen citrate, trisodium citrate, trisodium citrate dihydrate, potassium dihydrogen citrate, dipotassium hydrogen citrate, tripotassium citrate, lithium dihydrogen citrate, dilithium hydrogen citrate, and/or trilithium citrate. Even more preferred, however, are citric acid, sodium dihydrogen citrate, disodium hydrogen citrate, trisodium citrate, trisodium citrate dihydrate, potassium dihydrogen citrate, dipotassium hydrogen citrate and/or tripotassium citrate. However, most preferred are citric acid, sodium dihydrogen citrate, disodium hydrogen citrate, trisodium citrate and trisodium citrate dihydrate.

According to the invention, it is further preferred if the citrate solution contains, apart from the said citrate compound or the said citrate compounds, no additional, i.e. further non-citrate based substances which chelate $Ca^{2+}$ (so called $Ca^{2+}$ chelators), A preferred embodiment of the present invention therefore relates to the use of a citrate solution for the affinity-chromatographic removal of CRP from biological fluids by means of a column material functionalized with ω-phosphonooxyalkyl ammonium groups and/or ω-ammoniumalkoxy-hydroxy-phosphoryloxy groups, wherein the citrate solution contains no $Ca^{2+}$ chelators, which are not chemically based on citrate compounds. Possible examples of $Ca^{2+}$ chelators which are not chemically based on citrate compounds and thus are not preferred are EDTA (ethylenediaminetetraacetic acid), EGTA (ethylene glycol bis (aminoethyl ether)-N,N,N',N'-tetraacetic acid), BAPTA (1,2-bis(ω-aminophenoxy)ethane-N,N,N',N'-tetraacetic acid) and oxalates.

A preferred embodiment of the present invention therefore relates to the use of a citrate solution for the affinity-chromatographic removal of CRP from biological fluids by means of a column material functionalized with ω-phosphonooxyalkyl ammonium groups and/or ω-ammoniumalkoxy-hydroxy-phosphoryloxy groups, wherein the citrate solution contains at least one of the citrate compounds from the group comprising or consisting of citric acid, sodium dihydrogen citrate, disodium hydrogen citrate, trisodium citrate, trisodium citrate dihydrate, potassium dihydrogen citrate, dipotassium hydrogen citrate, tripotassium citrate, lithium dihydrogen citrate, dilithium hydrogen citrate, trilithium citrate, ammonium dihydrogen citrate, diammonium hydrogen citrate, triammonium citrate, tricalcium dicitrate (calcium citrate), trimagnesium dicitrate (magnesium citrate) and/or partial citrate esters, wherein the citrate solution contains no additional $Ca^{2+}$ chelators apart from the citrate compound(s).

Therefore, according to the invention, it is furthermore preferred if the citrate solution does not contain EDTA (ethylenediaminetetraacetic acid), EGTA (ethyleneglycol bis(aminoethyl ether)-N,N,N',N'-tetraacetic acid), BAPTA (1,2-aminophenoxy)ethane-N,N,N',N'-tetraacetic acid) or oxalate.

In addition to the citrate compounds listed above, the citrate solution may contain additional substances which, however, do not have any chelating properties. For example, further substances are possible as additives which contribute to the osmolarity of the citrate solution being approximately equal to the osmolarity of the biological fluid, i.e. for example of the blood or blood plasma. Such substances for adjusting the osmolarity comprise inorganic salts such as, for example, sodium chloride, potassium chloride, but also sugars such as glucose, dextrose (D-glucose), fructose and sucrose or heparin. The terms dextrose and D-glucose are equivalent, and can therefore be used synonymously herein.

Likewise, further substances are possible as additives which serve to adjust the pH value of the citrate solution to a predetermined value, e.g. the pH value of the biological fluid (thus for example of the blood or blood plasma). Here, it is for example possible that the additional substance contained together with the citrate compound forms a buffer system, by means of which the pH value of the citrate solution can be adjusted and slight fluctuations in the pH value can be compensated. If the citrate solution contains a buffer system of citrate compound and a non-citrate buffer substance, the term "citrate-containing buffer" is also used. Possible examples of added buffering substances which are not citrate compounds (i.e. non-citrate buffer substances) comprise disodium hydrogen phosphate, sodium dihydrogen phosphate, dipotassium hydrogen phosphate, potassium dihydrogen phosphate, lactate and acetate.

Possible examples of buffer systems from a citrate compound and a non-citrate buffer substance, i.e. a citrate solution according to the invention in the form of a citrate-containing buffer, is the combination of citric acid with disodium hydrogen phosphate, sodium dihydrogen phosphate, dipotassium hydrogen phosphate or potassium dihydrogen phosphate. However, the combination of citric acid with disodium hydrogen phosphate is particularly preferred.

However, if the citrate solutions contain two different citrate compounds, which together also form a buffer system, the term "citrate buffer" is also used.

Possible examples of buffer systems from two different citrate compounds, i.e. a citrate solution according to the invention in form of a citrate buffer, is the combination of citric acid with sodium hydrogen citrate, disodium hydrogen citrate, trisodium citrate, potassium dihydrogen citrate, dipotassium hydrogen citrate or tripotassium citrate;

the combination of sodium dihydrogen citrate with disodium hydrogen citrate, trisodium citrate, dipotassium hydrogen citrate or tripotassium citrate;

the combination of potassium dihydrogen citrate with disodium hydrogen citrate, trisodium citrate, dipotassium hydrogen citrate or tripotassium citrate;

the combination of disodium hydrogen citrate with trisodium citrate or tripotassium citrate; the combination of dipotassium hydrogen citrate with trisodium citrate or tripotassium citrate.

However, the combination of citric acid with trisodium citrate as citrate solution in form of a citrate buffer is particularly preferred.

Of course, it is also conceivable to add further substances to the citrate solution containing two different citrate compounds (i.e. a citrate buffer) for adjusting the osmolarity.

According to the invention, it is preferred if the citrate solution consists merely of water, one or more of the above-mentioned citrate compounds, as well as optionally of one or more of the above-mentioned compounds for adjusting the osmolarity (also referred to as "osmolytics") and/or optionally of one or more of the above-mentioned non-citrate buffer substances.

A further embodiment of the present invention thus relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution consist of water and at least one of the citrate compounds from the group comprising or consisting of citric acid, sodium dihydrogen citrate, disodium hydrogen citrate, trisodium citrate, trisodium citrate dihydrate, potassium hydrogen citrate, dipotassium hydrogen citrate, tripotassium citrate, lithium dihydrogen citrate, dilithium hydrogen citrate, trilithium citrate, ammonium dihydrogen citrate, diammonium hydrogen citrate, triammonium citrate, tricalcium dicitrate (calcium citrate), trimagnesium dicitrate (magnesium citrate), and/or partial citrate ester; and (optionally) at least one of the compounds from the group comprising or consisting of sodium chloride, potassium chloride, glucose, fructose and sucrose, and/or (optionally) at least one of the compounds from the group comprising or consisting of disodium hydrogen phosphate, sodium dihydrogen phosphate, dipotassium hydrogen phosphate, potassium dihydrogen phosphate, lactate and acetate.

A further preferred embodiment of the present invention therefore relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution consists of citric acid, trisodium citrate and water.

A particularly preferred embodiment of the present invention thus relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution contains 38 mM citric acid, 74.8 mM trisodium citrate, and water.

A preferred embodiment of the present invention thus relates to the use of a citrate solution for affinity-chromatographic removal of CRP from biological fluids by means of a column material functionalized with a ω-phosphonooxyalkyl ammonium groups and/or with ω-ammoniumalkoxyhydroxy-phosphoryloxy groups, wherein the citrate solution consist of citric acid, trisodium citrate, D-glucose and water.

A citrate solution consisting of citric acid, trisodium citrate, D-glucose and water is also referred to as "acid-citrate-dextrose-solution (ACD-solution).

Preferred variants of the citrate solution used according to the invention relate to ACD-solutions which contain between 22.9 mM and 38.0 mM citric acid, between 44.9 mM and 74.8 mM trisodium citrate, between 74.2 mM and 123.6 mM D-glucose and water.

A particularly preferred variant of the citrate solution used according to the invention relates to a ACD-solution which contains 38 mM citric acid, 74.8 mM trisodium citrate, 123.6 mM D-glucose and water. This is also referred to as "ACD-A solution".

A particularly preferred embodiment of the present invention thus relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution contains 38 mM citric acid, 74.8 mM trisodium citrate, 123.6 mM D-glucose and water.

A further preferred embodiment of the present invention thus relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution consists of citric acid, trisodium citrate, sodium hydrogen phosphate, D-glucose and water.

A citrate solution consisting of citric acid, trisodium citrate, sodium hydrogen phosphate, D-glucose and water is also referred to as "citrate-phosphate-dextrose-solution (CPD)".

A preferred variant of the citrate solution used according to the invention relates to a CPD-solution which contains 15.6 mM citric acid, 89.4 mM trisodium citrate, 128.7 mM D-glucose, 16.1 mM sodium hydrogen phosphate and water.

A particularly preferred embodiment of the present invention thus relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution contains 15.6 mM citric acid, 89.4 mM trisodium citrate, 128.7 mM D-glucose, 16.1 mM sodium hydrogen phosphate and water.

A further preferred embodiment of the present invention thus relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution consists of citric acid, trisodium citrate, sodium hydrogen phosphate, D-glucose, adenine and water.

A citrate solution consisting of citric acid, trisodium citrate, sodium hydrogen phosphate, D-glucose, adenine and water is also referred to as "citrate-phosphate-dextrose-solution with adenine (CPDA)".

A preferred variant of the citrate solution used according to the invention thus relates to a CPDA-solution which contains 15.6 mM citric acid, 89.4 mM trisodium citrate, between 128.7 mM and 160.9 mM D-glucose, 16.1 mM sodium hydrogen phosphate, 2 mM adenine and water. A further preferred variant of the citrate solution used according to the invention relates to CPDA-solution which contains 15.6 mM citric acid, 89.4 mM trisodium citrate, 128.7 mM D-glucose, 16.1 mM sodium hydrogen phosphate, 2 mM adenine and water. A particularly preferred variant of the citrate solution used according to the invention relates to a CPDA-solution which contains 15.6 mM citric acid, 89.4 mM trisodium citrate, 160.9 mM D-glucose, 16.1 mM sodium hydrogen phosphate, 2 mM adenine and water.

A particularly preferred embodiment of the present invention thus relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution contains 15.6 mM citric acid, 89.4 mM trisodium citrate, between 128.7 mM and 160.9 mM D-glucose, 16.1 mM sodium hydrogen phosphate, 2 mM adenine and water.

According to some embodiments of the present invention it is preferred, if the citrate solution contains no metal salts with multivalent, i.e. divalent or trivalent cations. Thus, in a further preferred embodiment of the present invention the citrate solution contains no calcium salts. In a further preferred embodiment of the present invention the citrate solution contains no magnesium salts or at least a magnesium salt in a concentration of at most 1 mM.

In other words, according to some embodiments of the present invention it is preferred if citrate solution contains only metal salts with monovalent cations.

Citrate Concentration and Dilution with Biological Fluid

A preferred embodiment of the present invention thus relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution have a total concentration of citrate in a range from 50 mM to 200 mM, preferred from 60 mM to 150 mM, more preferred 70 mM to 120 mM, more preferred 75 mM to 115 mM, and most preferred from 74.8 mM to 113 mM.

A preferred embodiment of the present invention thus also relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution have a total concentration of citrate of preferably 50 mM, of 150 mM, of 200 mM, more preferred of 60 mM, more preferred of 120 mM, more preferred of 115 mM, more preferred of 70 mM, more preferred of 75 mM, more preferred of 74.8 mM, and most preferred of 113 mM.

Of course, not only the concentration of citrate in the actual citrate solution is important but above all the final concentration in the mixture of citrate solution and biological fluid, i.e. for example blood or blood plasma. Therefore, the dilution of the citrate solution used is also important.

Thus, the present invention also relates to the use of a citrate solution for affinity-chromatographic removal of CRP from biological fluids by means of a column material functionalized with a ω-phosphonooxyalkyl ammonium groups and/or with ω-ammoniumalkoxy-hydroxy-phosphoryloxy groups, wherein the biological fluid is mixed with the citrate solution prior to CRP removal.

The present invention therefore also relates to the use of a citrate solution as binding buffer (or binding solution) for affinity-chromatographic removal of CRP from biological fluids by means of a column material functionalized with a ω-phosphonooxyalkyl ammonium groups and/or with ω-ammoniumalkoxy-hydroxy-phosphoryloxy groups, wherein the biological fluid is mixed with the citrate solution prior to CRP removal.

The present invention thus relates to the use of a citrate solution for affinity-chromatographic removal of CRP from biological fluids, wherein the affinity-chromatographic removal of CRP is performed by (a $Ca^{2+}$-dependent) binding of CRP to a column material functionalized with ω-phosphonooxyalkyl ammonium groups and/or with ω-ammoniumalkoxy-hydroxy-phosphoryloxy groups, and wherein the biological fluid is mixed with the citrate solution prior to CRP removal.

Following the mixing of the citrate solution with the biological fluid (i.e. for example blood or blood plasma) the mixture of citrate solution and biological fluid is applied onto the column material which has been functionalized with ω-phosphonooxyalkyl ammonium groups and/or with ω-ammoniumalkoxy-hydroxy-phosphoryloxy groups, so that a ($Ca2+$-dependent) binding of CRP to the functionalized column material occurs.

The present invention thus also relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution is diluted in a range from 1:50 to 1:5, preferably from 1:40 to 1:10, preferably from 1:30 to 1:20, preferably from 1:20 to 1:15, preferably from 1:15 to 1:10 with the biological fluid.

The present invention thus also relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution is diluted 1:50, preferred 1:45, further preferred 1:40, preferred 1:35, preferred 1:30, preferred 1:25, further preferred 1:20, further preferred 1:15, further preferred 1:10, preferred 1:5 with the biological fluid.

A preferred embodiment of the present invention thus relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups in a dilution in a range from 1:50 to 1:5 with the biological fluid.

A preferred embodiment of the present invention thus also relates to the use of a citrate solution for affinity-chromatographic removal of CRP from biological fluids by means of a column material functionalized with ω-phosphonooxy-alkyl ammonium groups and/or with ω-ammoniumalkoxy-hydroxy-phosphoryloxy groups, wherein the citrate solution have a total concentration of citrate in a range of 50 mM to 200 mM, preferred from 60 mM to 150 mM, more preferred 70 mM to 120 mM, more preferred 75 mM to 115 mM, and most preferred from 74.8 mM to 113 mM; and wherein the citrate solution is diluted in a range from 1:50 to 1:5, preferably from 1:40 to 1:10, preferably from 1:30 to 1:20, preferably from 1:20 to 1:15, preferably from 1:15 to 1:10 with the biological fluid.

A further preferred embodiment of the present invention thus also relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution have a total concentration of citrate in a range of 70 mM to 120 mM; and wherein the citrate solution is diluted in a range of 1:50 to 1:5 with the biological fluid.

It is of course also conceivable that citrate solutions containing a lower or higher citrate concentration than those described in the preceding paragraphs are used. Accordingly, of course, the degree of dilution with the biological fluid would have to be correspondingly reduced (at lower citrate concentrations) or increased (at higher citrate concentrations). However, the citrate concentrations and dilutions described in the preceding paragraphs have proved to be particularly advantageous in conjunction with the use according to the invention of a citrate solution for the affinity-chromatographic removal of CRP from biological fluids.

Since the pH of a solution has a substantial influence on the dissociation of acids and bases (thus also for example of citric acid), and thus also influence the binding of $Ca^{2+}$ in the present case, the pH value of the used citrate solution is an important aspect of the present invention.

The present invention thus also relates to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, wherein the citrate solution have a pH value in range from pH 4.0 to pH 7.0, preferred from pH 4.5 to pH 6.5, more preferred from pH 4.7 to pH 6.0, more preferred from pH 4.9 to pH 5.8, more preferred from pH 5.0 to pH 5.6, and most preferred from pH 5.0 to pH 5.5.

$Ca^{2+}$-Dependent Ligands for CRP

As already mentioned several times, for the affinity-chromatographic removal of CRP from biological fluids, for example from blood or blood plasma, a column material is used which contains phosphocholine and/or phosphoethanolamine or its derivatives, whereby a $Ca^{2+}$-dependent binding of CRP to the said functionalized column material is possible.

For this purpose, phosphocholine, phosphoethanolamine or its derivatives is immobilized on a column material. This usually takes place via an organic linker group, via which the phosphocholine, phosphoethanolamine or their derivatives is adsorptively or even more preferably covalently linked to the column material. This results in a so-called "functionalized column material", wherein the chemical group responsible for the $Ca^{2+}$-dependent binding of CRP is exposed to the outside, so that CRP which is located in a biological fluid, also has access to said chemical group.

In other words, the term "functionalized column material" as used herein refers to a column material for affinity chromatography which is provided with a functional chemical group. In this case, the functional chemical group can be connected to the column material via adsorptive or ionic interactions but preferably via a covalent bond. It is, of course, important that the functional chemical group is linked to the column material such that the functional group is active and exposed so that its functionality is retained. As a result, it is possible for the group (here: ω-phosphonooxyalkyl ammonium group and/or ω-ammoniumalkoxy-hydroxy-phosphoryloxy group) attached to the column material to interact with a ligand (here: CRP) from the sample (here: biological liquid such as blood or blood plasma) or to bind it.

Depending on whether the phosphocholine, phosphoethanolamine or its derivative is linked to the column material via an organic linker via the ammonium group or via the phosphate group, a distinction is made between a column material which has been functionalized with an ω-phosphonooxyalkyl ammonium group (linkage via the ammonium group), and a column material functionalized with an ω-ammoniumalkoxy-hydroxy-phosphoryloxy group (linkage via the phosphate group).

The linkage with the column material (optionally by means of an organic linker) is shown in the formulas (I) and (II) listed below via a dashed line either on the nitrogen atom of the ammonium group or on the oxygen atom of the phosphate group.

The term "ω-phosphonooxyalkyl ammonium group" as used herein can be used similarly as "omega-phosphonooxyalkyl ammonium" and describes compounds of the following general formula (I)

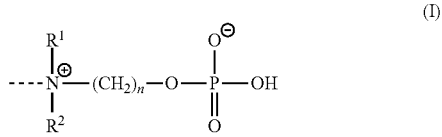
(I)

wherein
n is selected from 2 and 3;
$R^1$ and $R^2$ are independently selected from: —H, —CH$_3$, —C$_2$H$_5$, —C$_3$H$_7$, —C$_4$H$_9$, —C$_5$H$_{11}$, —C$_6$H$_{13}$, or $R^1$ and $R^2$ together with the nitrogen atom to which they are attached form a heterocycle selected from:

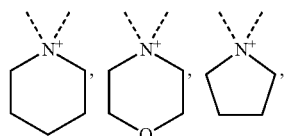

wherein one or more hydrogen atom(s) can be replaced by (a) fluorine atom(s).

The present invention thus also directed to the use of a citrate solution for affinity-chromatographic removal of CRP from biological fluids by means of a column material functionalized with ω-phosphonooxyalkyl ammonium groups and/or with ω-ammoniumalkoxy-hydroxy-phosphoryloxy groups, characterized in that the ω-phosphonooxyalkyl ammonium groups have the following general formula (I):

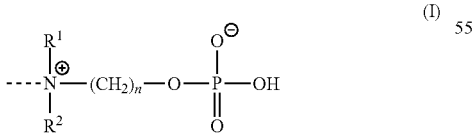
(I)

wherein
n is selected from 2 and 3;
$R^1$ and $R^2$ are independently selected from: —H, —CH$_3$, —C$_2$H$_5$, —C$_3$H$_7$, —C$_4$H$_9$, —C$_5$H$_{11}$, —C$_6$H$_{13}$, or $R^1$ and $R^2$ together with the nitrogen atom to which they are attached can form a heterocycle selected from:

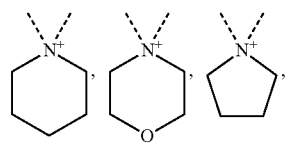

wherein one or more hydrogen atom(s) can be replaced by (a) fluorine atom(s).

Preferred ω-phosphonooxyalkyl ammonium groups comprise compounds of the general formula (I):

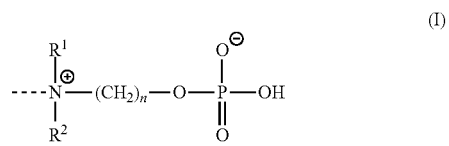
(I)

wherein
n=2 or 3;
$R^1$ and $R^2$ are independently selected from: —H, —CH$_3$, —C$_2$H$_5$, —C$_3$H$_7$, or $R^1$ and $R^2$ together with the nitrogen atom to which they are attached can form a heterocycle selected from:

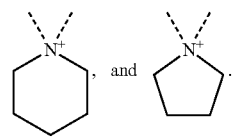

Particularly preferred ω-phosphonooxyalkyl ammonium groups comprise compounds of the general formula (I):

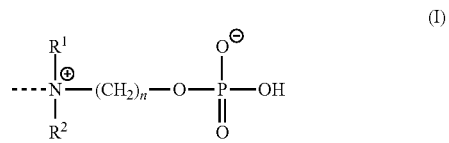
(I)

wherein
n is 2;
$R^1$ and $R^2$ are selected from: —H, —CH$_3$, —C$_2$H$_5$, and particularly preferred from —CH$_3$, and —C$_2$H$_5$, or $R^1$ and $R^2$ together with the nitrogen atom to which they are attached can form a heterocycle selected from:

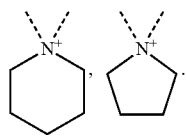

Preferred compounds containing an ω-phosphonooxyalkyl ammonium group as described above and suitable for the functionalization of a corresponding column material comprise for example:
2-[2-(2-aminoethoxy)ethyl-diethyl-ammonio]ethyl hydrogen phosphate, 2-[4-[2-(2-aminoethoxy)ethyl]morpholin-4-ium-4-yl]ethyl hydrogen phosphate, 2-[1-[2-(2-aminoethoxy)ethyl]piperidin-1-ium-1-yl]ethyl-hydrogen phosphate, 2-[2-(2-aminoethoxy)ethyl-dimethyl-ammonio]ethyl hydrogen phosphate, 2-[3-aminopropyl-(dimethyl)ammonio]ethyl hydrogen phosphate, 2-[dimethyl(4-sulfanylbutyl)ammonio]ethyl hydrogen phosphate, 2-[4-azidobutyl(dimethyl)ammonio]ethyl hydrogen phosphate, 2-[dimethyl(pent-4-ynyl)ammonio]ethyl hydrogen phosphate, 2-[3-(6-aminohexanoyl-amino)propyl-diethyl-ammonio]ethyl hydrogen phosphate, 2-[1-[2-[2-(6-aminohexanoyl-amino)ethoxy]ethyl]piperidin-1-ium-1-yl]ethyl hydrogen phosphate, 2-[4-[2-[2-[3-(6-aminohexanoylamino)propanoylamino]ethoxy]ethyl]morpholin-4-ium-4-yl]ethyl hydrogen phosphate, 2-[1-[2-[2-[6-(6-aminohexanoylamino)hexanoylamino]ethoxy]ethyl]pyrrolidin-1-ium-1-yl]ethyl hydrogen phosphate, 2-[2-allyloxyethyl(dimethyl)ammonio]ethyl hydrogen phosphate, 2-[2-allyloxyethyl(diethyl)ammonio]ethyl hydrogen phosphate, 2-[4-(2-allyloxyethyl)morpholin-4-ium-4-yl]ethyl hydrogen phosphate, 2-[1-(2-allyloxyethyl)piperidin-1-ium-1-yl]ethyl hydrogen phosphate, 2-[2-[2-(6-aminohexanoylamino)ethoxy]ethyl-dimethyl-ammonio]ethyl hydrogen phosphate, 2-[2-[2-[3-(6-aminohexanoylamino)propanoylamino]ethoxy]ethyl-dimethyl-ammonio]ethyl hydrogen phosphate, 2-[3-azidopropyl(dimethyl)ammonio]ethyl hydrogen phosphate, 2-[dimethyl-[2-[2-(prop-2-ynoxycarbonylamino)ethoxy]ethyl]ammonio]ethyl hydrogen phosphate, 2-[2-[2-(allyloxycarbonylamino)ethoxy]ethyl-dimethyl-ammonio]ethyl hydrogen phosphate, 2-[2-[2-[6-(allyloxycarbonylamino)hexanoylamino]ethoxy]ethyl-dimethyl-ammonio]ethyl hydrogen phosphate, 2-[2-(6-aminohexanoylamino)ethyl-dimethyl-ammonio]ethyl hydrogen phosphate, 2-[dimethyl-[3-[6-(prop-2-ynoxycarbonylamino)-hexanoylamino]propyl]ammonio]ethyl hydrogen phosphate, and 2-[3-(6-aminohexanoylamino)propyl-dimethyl-ammonio]ethyl hydrogen phosphate.

The term "ω-ammoniumalkoxy-hydroxy-phosphoryloxy groups" as used herein can be used similarly as "omega-ammoniumalkoxy-hydroxy-phosphoryloxy groups" and describes compounds of the following general formula (II)

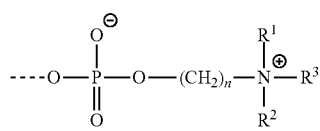

(II)

wherein
n is selected from 2 and 3;
$R^1$, $R^2$ and $R^3$ are independently selected from: —H, —$CH_3$, —$C_2H_5$, —$C_3H_7$, —$C_4H_9$, —$C_5H_{11}$, —$C_6H_{13}$, or $R^1$ and $R^2$ together with the nitrogen atom to which they are attached can form a heterocycle selected from:

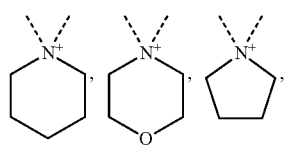

and
$R^3$ is selected from: —H, —$CH_3$, —$C_2H_5$, —$C_3H_7$, —$C_4H_9$, —$C_5H_{11}$, —$C_6H_{13}$, and preferably —H;

wherein one or more hydrogen atom(s) can be replaced by (a) fluorine atom(s).

Preferred "ω-ammoniumalkoxy-hydroxy-phosphoryloxy groups" comprise compounds of the general formula (II)

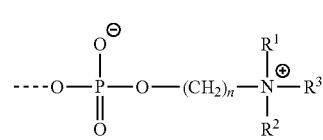

(II)

wherein
n is selected from 2 and 3;
$R^1$, $R^2$ and $R^3$ are independently selected from: —H, —$CH_3$, —$C_2H_5$, —$C_3H_7$, or $R^1$ and $R^2$ together with the nitrogen atom to which they are attached can form a heterocycle selected from:

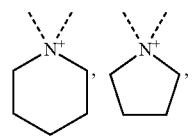

and
$R^3$ is —H.

Within the scope of the present invention, it is particularly preferred if the ω-ammoniumalkoxy-hydroxy-phosphoryloxy group is an ω-trialkylammoniumalkoxy-hydroxy-phosphoryloxy group.

Therefore, particularly preferred ω-ammoniumalkoxy-hydroxy-phosphoryloxy groups comprise compounds of the general formula (II)

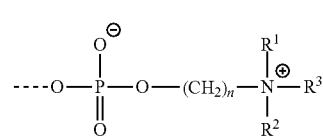

(II)

wherein
n=2;
and $R^1$, $R^2$ and $R^3$ is selected from: —H, —$CH_3$, —$C_2H_5$
and particularly preferred from —$CH_3$ and —$C_2H_5$.

It is also particularly preferred if the ω-ammoniumalkoxy-hydroxy-phosphoryloxy groups are ω-trimethylammoniumethoxy-hydroxy-phosphoryloxy groups or ω-trimethylammoniumpropoxy-hydroxy-phosphoryloxy groups.

Preferred compounds containing an ω-ammoniumalkoxy-hydroxy-phosphoryloxy group as described above and suitable for the functionalization of a corresponding column material comprise for example: p-aminophenylphosphocholine (APPC), 4-[[hydroxy[2-(trimethylammonio)ethoxy]phosphinyl]oxy]benzenediazonium(p-diazonium phenylphosphocholine) or p-nitrophenyl-6-(O-phosphocholine)hydroxyhexanoate.

The present invention is also directed to the use of a citrate solution for the affinity-chromatographic removal of CRP from biological fluids by means of a column material functionalized with ω-phosphonooxyalkyl ammonium groups and/or ω-ammoniumalkoxy-hydroxy-phosphoryloxy groups, characterized in that the ω-ammoniumalkoxy-hydroxy-phosphoryloxy groups have the following general formula (II)

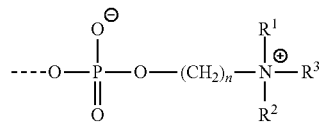
(II)

wherein
n is selected from 2 and 3;
R$^1$, R$^2$ and R$^3$ are independently selected from: —H, —CH$_3$, —C$_2$H$_5$, —C$_3$H$_7$, —C$_4$H$_9$, —C$_5$H$_{11}$, —C$_6$H$_{13}$, or R$^1$ and R$^2$ together with the nitrogen atom to which they are attached can form a heterocycle selected from:

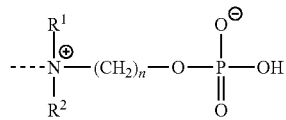

and
R$^3$ is selected from: —H, —CH$_3$, —C$_2$H$_5$, —C$_3$H$_7$, —C$_4$H$_9$, —C$_5$H$_{11}$, —C$_6$H$_{13}$, and preferably —H;
wherein one or more hydrogen atom(s) can be replaced by (a) fluorine atom(s).

The present invention is thus also directed to the use of a citrate solution for the affinity-chromatographic removal of CRP from biological fluids by means of a column material functionalized with ω-phosphonooxyalkyl ammonium groups and/or ω-ammoniumalkoxy-hydroxy-phosphoryloxy groups, characterized in that the ω-phosphonooxyalkyl ammonium groups have the following general formula (I)

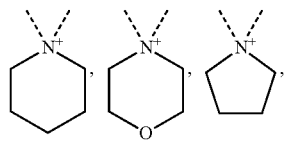
(I)

wherein
n is selected from 2 and 3;
R$^1$ and R$^2$ are independently selected from: —H, —CH$_3$, —C$_2$H$_5$, —C$_3$H$_7$, —C$_4$H$_9$, —C$_5$H$_{11}$, —C$_6$H$_{13}$, or R$^1$ and R$^2$ together with the nitrogen atom to which they are attached form a heterocycle selected from:

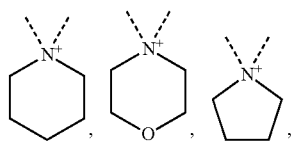

wherein one or more hydrogen atom(s) can be replaced by (a) fluorine atom(s),
and characterized in that the ω-ammoniumalkoxy-hydroxy-phosphoryloxy groups have the following general formula (II)

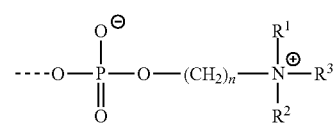
(II)

wherein
n is selected from 2 and 3;
R$^1$, R$^2$ and R$^3$ are independently selected from: —H, —CH$_3$, —C$_2$H$_5$, —C$_3$H$_7$, —C$_4$H$_9$, —C$_5$H$_{11}$, —C$_6$H$_{13}$, or R$^1$ and R$^2$ together with the nitrogen atom to which they are attached can form a heterocycle selected from:

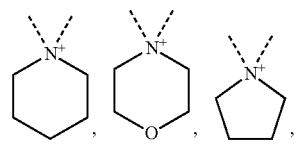

and
R$^3$ is selected from: —H, —CH$_3$, —C$_2$H$_5$, —C$_3$H$_7$, —C$_4$H$_9$, —C$_5$H$_{11}$, —C$_6$H$_{13}$, and preferably —H;
wherein one or more hydrogen atom(s) can be replaced by (a) fluorine atom(s).

Therefore, the present invention also relates to the use of citrate solution for affinity-chromatographic removal of CRP from biological fluids, wherein the affinity-chromatographic removal of CRP is performed by (a Ca$^{2+}$-dependent) binding of CRP to a column material functionalized with ω-phosphonooxyalkyl ammonium groups and/or with ω-ammoniumalkoxy-hydroxy-phosphoryloxy groups, wherein the ω-phosphonooxyalkyl ammonium groups have the following general formula (I)

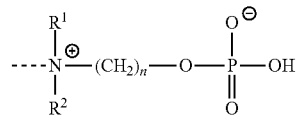
(I)

wherein
n is selected from 2 and 3;
R$^1$ and R$^2$ are independently selected from: —H, —CH$_3$, —C$_2$H$_5$, —C$_3$H$_7$, —C$_4$H$_9$, —C$_5$H$_{11}$, —C$_6$H$_{13}$, or R$^1$ and R$^2$ together with the nitrogen atom to which they are attached form a heterocycle selected from:

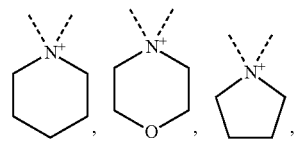

wherein one or more hydrogen atom(s) can be replaced by (a) fluorine atom(s).

The present invention is also directed to the use of citrate solution for affinity-chromatographic removal of CRP from biological fluids, wherein the affinity-chromatographic removal of CRP is performed by (a Ca$^{2+}$-dependent) binding of CRP to a column material functionalized with ω-phosphonooxyalkyl ammonium groups and/or with ω-ammoniumalkoxy-hydroxy-phosphoryloxy groups, wherein the ω-ammoniumalkoxy-hydroxy-phosphoryloxy groups have the following general formula (II)

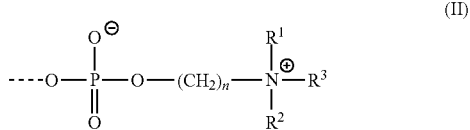
(II)

wherein
n is selected from 2 and 3;
R$^1$, R$^2$ and R$^3$ are independently selected from: —H, —CH$_3$, —C$_2$H$_5$, —C$_3$H$_7$, —C$_4$H$_9$, —C$_5$H$_{11}$, —C$_6$H$_{13}$, or R$^1$ and R$^2$ together with the nitrogen atom to which they are attached can form a heterocycle selected from:

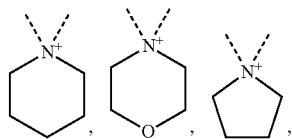

and
R$^3$ is selected from: —H, —CH$_3$, —C$_2$H$_5$, —C$_3$H$_7$, —C$_4$H$_9$, —C$_5$H$_{11}$, —C$_6$H$_{13}$, and preferably —H;
wherein one or more hydrogen atom(s) can be replaced by (a) fluorine atom(s).

Therefore, the present invention also relates to the use of citrate solution for affinity-chromatographic removal of CRP from biological fluids, wherein the affinity-chromatographic removal of CRP is performed by (a Ca$^{2+}$-dependent) binding of CRP to a column material functionalized with ω-phosphonooxyalkyl ammonium groups and/or with ω-ammoniumalkoxy-hydroxy-phosphoryloxy groups, wherein the ω-phosphonooxyalkyl ammonium groups have the following general formula (I)

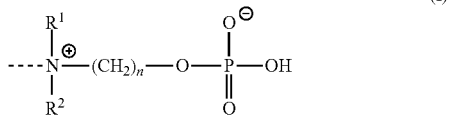
(I)

wherein
n is selected from 2 and 3;
R$^1$ and R$^2$ is independently selected from: —H, —CH$_3$, —C$_2$H$_5$, —C$_3$H$_7$, —C$_4$H$_9$, —C$_5$H$_{11}$, —C$_6$H$_{13}$, or R$^1$ and R$^2$ together with the nitrogen atom to which they are attached can form a heterocycle selected from:

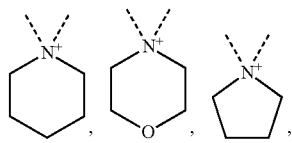

wherein one or more hydrogen atom(s) can be replaced by (a) fluorine atom(s);

and wherein the ω-ammoniumalkoxy-hydroxy-phosphoryloxy groups have the following general formula (II)

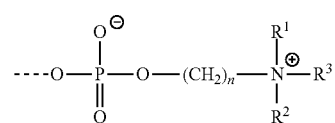
(II)

wherein
n is selected from 2 and 3;
R$^1$, R$^2$ and R$^3$ are independently selected from: —H, —CH$_3$, —C$_2$H$_5$, —C$_3$H$_7$, —C$_4$H$_9$, —C$_5$H$_{11}$, —C$_6$H$_{13}$, or R$^1$ and R$^2$ together with the nitrogen atom to which they are attached can form a heterocycle selected from:

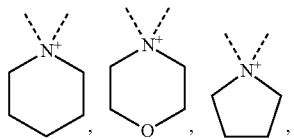

and
R$^3$ is selected from: —H, —CH$_3$, —C$_2$H$_5$, —C$_3$H$_7$, —C$_4$H$_9$, —C$_5$H$_{11}$, —C$_6$H$_{13}$, and preferably —H;
wherein one or more hydrogen atom(s) can be replaced by (a) fluorine atom(s).

In one possible embodiment of the present invention, the ω-ammoniumalkoxy-hydroxy-phosphoryloxy group is linked via a phosphoester bond to a hydroxy group of a glycerol molecule (as an organically linker), wherein the resulting glycerol ester is then linked to the column material via a second hydroxy group of the glycerol. In such an embodiment, it is also possible that the remaining third hydroxy group of the glycerol is either esterified with a fatty acid or esterified with a second ω-ammoniumalkoxy-hydroxy-phosphoryloxy group. Moreover, the position of the respective esterification on the glycerol molecule can vary. Suitable fatty acids are common saturated, monoolefinic, polyolefinic, monoacetylenic, unsaturated linear and/or branched fatty acids having 8 to 28 carbon atoms. Preferred fatty acid residues are palmitic acid, arachidonic acid, oxovaleric acid, glutaric acid, epoxyisoprostane and stearic acid.

Column Material

For the preparation of the column material functionalized with ω-phosphonooxyalkyl ammonium groups and/or with ω-ammoniumalkoxy-hydroxy-phosphoryloxy groups, in principle, all inert chromatography or column materials are suitable as materials which, in particular, do not react with blood or blood plasma, or alter or contaminate the blood or blood plasma such that the blood or blood plasma after contact with the column material can no longer be injected into a patient. The column materials of the present invention comprise, but are not limited to: Eupergite®, polyvinylpyrrolidone (PVP), polysulfone (PS), polyethersulfone (PES), polyarylethersulfone (PAES), polyacrylate, methacrylate, methacrylate resins such as poly(methyl methacrylate) (PMMA) and poly(glycidyl methacrylate) (PGMA), poly(hydroxy methacrylate), polystyrene (PS), polytetrafluoroethylene (PTFE), polyacrylamide, polyacrolein, acrylonitrile butadiene styrene (ABS), polyacrylonitrile (PAN), polyurethane (PU), Sepharose®, acrylic beads, agarose, cellulosic matrices, polyethylene glycol (PEG), alginate, carrageenan, chitin, starch, nitrocellulose, ceramic matrices, glass beads and/or solid phase silicas or mixtures and/or derivatives of these substances. The solid-phase silica matrix can comprise almost any form of particulate silica, including amorphous silica, such as colloidal silica, silica gel, precipitated silica, and smoked or pyrogenic silica; microcrystalline silicas such as diatomaceous earth; and crystalline silicas such as quartz. The silica has a particle size in the range of about 45 to 120 mesh (approximately 345 µm to 125 µm), preferably in the range of about 45 to 60 mesh (approximately 345 µm to 212 µm).

Often, for the functionalization with ω-phosphonooxyalkyl ammonium groups and/or with ω-ammoniumalkoxy-hydroxy-phosphoryloxy groups, a column material is used which has already been "pre-functionalized", i.e. has been provided with a chemical group which then in turn allows the covalent attachment of the ω-phosphonooxyalkyl ammonium groups and/or the ω-ammoniumalkoxy-hydroxy-phosphoryloxy groups.

Such a "pre-functionalization" of a column material is achieved by methods well known to a skilled in the art (*Chin. J Chem.* 2012, 30, 2473, Polym. Int. 2013, 62, 991). In addition, some already "pre-functionalized" column materials are commercially available such as Toyopearl® AF-epoxy, Toyopearl® AF-amino, Toyopearl® AF-tresyl, TSKgel® tresyl, epoxy-activated Sepharose® 6B (GE Healthcare Life Sciences), CNBr-activated Sepharose® 4 fast flow (GE Healthcare Life Sciences), ECH Sepharose® 4B (GE Healthcare Life Sciences), NHS-activated Sepharose® 4 fast flow (GE Healthcare Life Sciences), terminal vinylsulfone activated Sepharose® 4 fast flow (Affiland), aldehyde Separopore® (Agarose) 4B, ECH Separopore® (Agarose) 4B (Separopore), agaroses from Sterogene Bioseparations, Inc., e.g. Epoxy-Ultraflow-4 Agarose (Sterogene Bioseparations, Inc.), Epoxy-Ultraflow-6 Agarose (Sterogene Bioseparations, Inc.), agaroses from emp Biotech GmbH, Epoxy-Ultraflow-4 Agarose (emp Biotech GmbH), Epoxy-Ultraflow-6 Agarose (emp Biotech GmbH), activated agaroses with any degree of cross-linking.

The use according to the invention of a citrate solution for the affinity-chromatographic removal of CRP from biological fluids by means of a column material functionalized with ω-phosphonooxyalkyl ammonium groups and/or with ω-ammoniumalkoxy-hydroxy-phosphoryloxy groups is particularly suitable for the extracorporeal removal of CRP from blood or blood plasma for reanimation after cardiac arrest, as well as for the prophylaxis and/or treatment of cardiovascular diseases, wherein the cardiovascular diseases are, in particular, heart attack (myocardial infarction), stroke and pulmonary embolism. Also suitable is the use according to the invention of a citrate solution for the affinity-chromatographic removal of CRP from biological fluids by means of a column material functionalized with ω-phosphonooxyalkyl ammonium groups and/or with ω-ammoniumalkoxy-hydroxy-phosphoryloxy groups for the extracorporeal removal of CRP from blood or blood plasma for prophylaxis and/or treatment of overreactions of the immune system, wherein the overreactions of the immune system are selected from the group of chronic inflammations, rejection reactions during transplants and allergic reactions. The use of a citrate solution according to the present invention is therefore particularly suitable for the extracorporeal removal of CRP from blood or blood plasma for the prophylaxis and/or treatment of chronic inflammations selected from the group: gout, osteoarthritis, multiple sclerosis, chronic inflammatory intestinal diseases such as Crohn's disease, ulcerative colitis, rheumatoid arthritis, psoriatic arthritis, myasthenia gravis, Graves disease, autoimmune thyroiditis such as Hashimoto's thyroiditis and Ord's thyroiditis, psoriasis vulgaris, ankylosan spondylitis (Bechterew's disease), goodpasture syndrome and idiopathic thrombocytopenic purpura (ITP), lupus erythematosus, scleroderma, Sjögren's syndrome, Wegener's granulomatosis (Wegener's disease), polymyositis and dermatomyositis. Among the above-mentioned chronic inflammations there are some diseases which fall under the generic term rheumatoid diseases, such as rheumatoid arthritis, psoriatic arthritis, myasthenia gravis, Graves Disease, Hashimoto-thyroiditis, Ord's thyroiditis, psoriasis vulgaris, ankylosan spondylitis, goodpasture syndrome and idiopathic thrombocytopenic purpura (ITP), lupus erythematosus, scleroderma, Sjögren syndrome, Wegener's granulomatosis (Wegener's disease), vasculitis, polymyalgia rheumatica, polymyositis and dermatomyositis.

Citrate is a good anticoagulant since it prevents the aggregation of blood platelets as well as complement activation. In particular, this is important when using plasma centrifuges. These require citrate since otherwise coagulation occurs. This is not feasible by pure anticoagulation with heparin. In addition, the citrate is rapidly metabolized in the liver in the citrate cycle. Patients are therefore not additionally systemically anticoagulated. This is of great interest, especially in infarction patients, since these are already strongly anticoagulated in the course of their standard infarction therapy (e.g. by acetylsalicylic acid, clopidogrel). Additional anticoagulation increases the risk of bleeding which is critical. In addition, the plasma centrifuge allows much less blood flow to be achieved than a membrane (filter)-based primary separation system. The usual or desired plasma flow is about 30 ml/minute. A membrane primary separation system requires a blood flow of approximately 150 to 200 ml/minute (efficiency is approximately 17%). A plasma centrifuge suffices≤60 ml/minute blood flow (efficiency approx. 87%). The smaller blood flow rates are much easier to realize, especially in elderly patients or those with little potential.

In addition, for a membrane-based primary separation system, a central access (e.g. catheter) is required that is very invasive and is dangerous in anticoagulated patients because of the risk of bleeding, whereas when a plasma centrifuge is used, usually a peripheral access via e.g. a larger injection cannula suffices, which does not present a bleeding problem.

EXAMPLES

Figure 1:
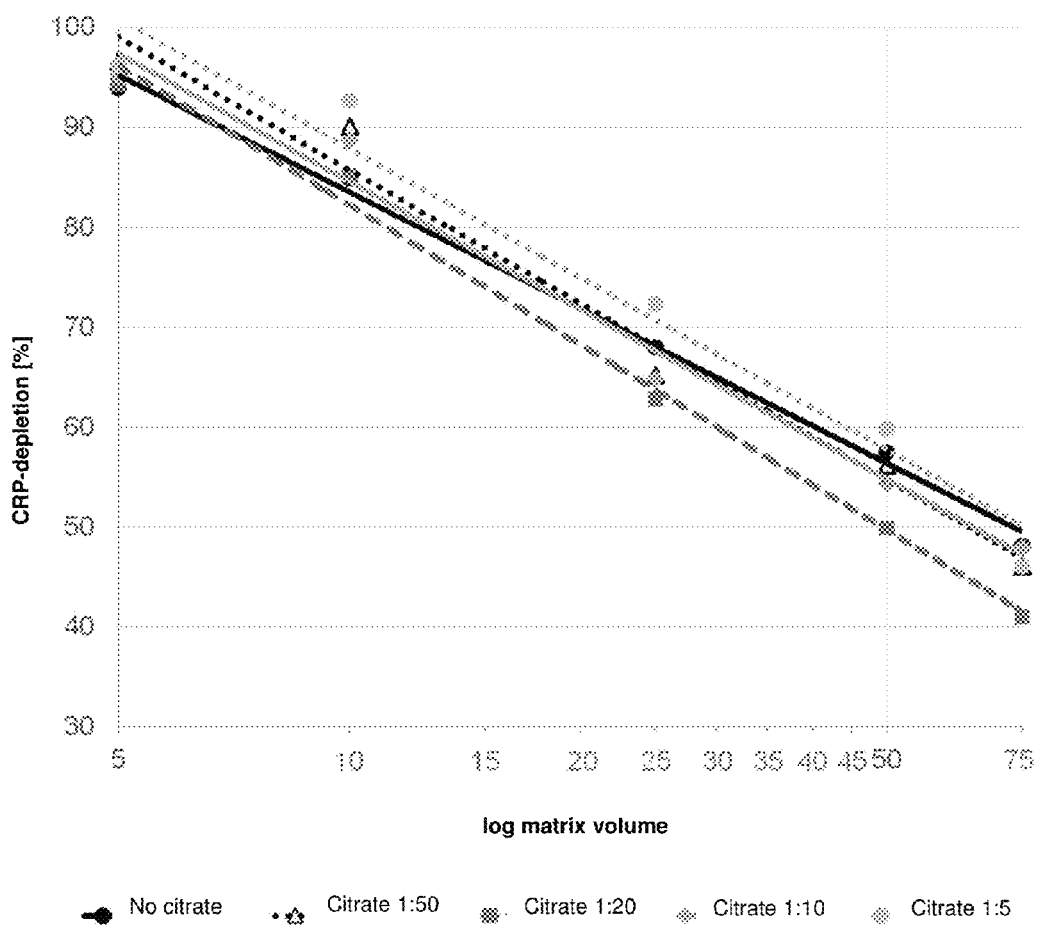
FIG. 1: The results of several chromatography runs for the purification of CRP are shown, the CRP depletion in % is plotted against the matrix volume in a semi-logarithmic representation. A citrate solution was added to human blood plasma with a CRP concentration of 50 mg/L, 1:5, 1:10, 1:20 or 1:50, and applied to a chromatography column containing 0.5 g of APPC-coupled epoxy-Ultraflow-4 Agarose (Sterogen) as a matrix. A sample without citrate addition served as a control. The column run was collected at a flow rate of 5, 10, 25, 50, and 75 matrix volumes in 1 ml fractions. The CRP concentration in the fractions was then determined and the CRP depletion in % was determined on the basis of the initial concentration of CRP (before the application). The data points represent mean values from at least two independent experiments.

The term "matrix volume" (also abbreviated as MV) as used herein refers to the volume of column material used in the respective affinity chromatography.

Example 1 Comparative Study on the Effect of Addition of Citrate Solution on the Affinity-Chromatographic Purification of CRP from Blood Plasma As a starting material, human blood plasma with a CRP concentration of approximately 50 mg/L was filtered using a 35 μm-filter, and optionally citrate solution was added (see below).

General Procedure of Affinity-Chromatography

For chromatography, a low-pressure chromatography system (BioLogic™ LP System, Bio-Rad, Munich Germany, catalogue number 731-8300), together with a column (Mobicol "Classic", MoBiTec GmbH, Göttingen, Germany, product number M1002) with a 35 μm-filter (MoBiTec GmbH, product number M523515) was used, which was equipped with 0.5 g of APPC-coupled agarose (epoxy-Ultraflow-4 agarose, Sterogene) as column material (1.6 mg APPC/ml), i.e. a column material with a sepharose-matrix to which the phosphocholine derivative p-aminophenylphosphocholine (APPC) was coupled. The column was equilibrated with 3 matrix volumes (MV) wash buffer (0.1 M Tris, 0.2 M NaCl, 2 mM $CaCl_2$, pH 8.0) and the flow was discarded.

The sample was then applied to the column. The flow of the column was divided into fractions of 1 ml each by means of a fraction collector (BioFrac™ Fraction Collector, Bio-Rad, catalogue number 741-0002) connected downstream of the column. The 1 ml fractions (also referred to as flow fractions) at a flow rate of 5 MV, 10 MV, 25 MV, 50 MV, 75 MV and 100 MV were collected while the remaining fractions were combined to form the so-called "flow pool".

The column was then washed with 25 MV wash buffer after the sample application. This was followed by elution of the CRP bound to the column by application of 7.5 MV elution buffer 1 (0.1 M Tris 0.2 M NaCl, 2 mM EDTA, pH 8.0). Here the eluate was fractionated and collected only when the UV absorption was above 0.01.

Subsequently, 5 MV elution buffer 2 (glycine buffer pH 2.8) was used to regenerate the column. If elution by the elution buffer 1 is not complete, proteins and in particular CRP may also be present in this fraction. Neutralization buffer (3.5 M Tris, pH 9.0) is added to this eluate, so that the CRP does not denature at the acid pH of the elution buffer 2 of 2.8. Finally, the column is washed again with 20 MV of the wash buffer.

The CRP content of the filtered starting material, of the flow pool and of the collected fractions was determined by means of a competitive and human-specific immunoassay (see, for example, Example 2).

Starting from the mean CRP concentration (also referred to as mean [CRP]) in the starting material, the percent CRP depletion was then determined for each fraction according to the following equation.

$$CRP-\text{Depletion (in \%)} = 100 - \left( \frac{\text{mean } [CRP] \text{ in fraction } X}{\text{mean } [CRP] \text{ in the starting material}} \times 100 \right)$$

Thus, conclusions were drawn about the retention of CRP through the column by means of the CRP concentration in a fraction, i.e. the flow from the column, taking into account the likewise determined CRP concentration in the starting material.

The total CRP quantity remaining on the column can be calculated by subtracting the total CRP amount of the flow-pool and the individual fractions from the total CRP amount in the starting material.

Influence of Citrate

In order to investigate the effect of citrate on the affinity-chromatographic purification of CRP from biological fluids e.g. blood plasma, by means of a column material functionalized with ω-phosphonooxyalkyl ammonium groups and/or with ω-ammoniumalkoxy-hydroxy-phosphoryloxy groups, the human blood plasma was mixed with citrate solution in different mixing ratios. The used citrate solution was as follows: 7.3 g of citric acid (anhydrous) per liter (i.e. 38 mM citric acid), 22.0 g of trisodium citrate dihydrate per liter (i.e., 74.8 mM trisodium citrate dihydrate), and 1 L with water. Experiments in which the citrate solution additionally contained 24.5 g of dextrose (monohydrate) per liter (i.e. 123.6 mM dextrose monohydrate) yielded identical results. The following mixing ratios were investigated:

The following mixing ratios were investigated:
1:50 i.e. 1 Part citrate solution+49 parts blood plasma
1:20 i.e. 1 Part of citrate solution+19 parts of blood plasma
1:10 i.e. 1 Part citrate solution+9 parts blood plasma
1:5 i.e. 1 Part citrate solution+4 parts blood plasma Human blood plasma without citrate addition served as reference sample. The citrate solution was added to the human blood plasma before the column using a gradient mixer.

For the reference sample (no citrate addition) and for each citrate concentration, two independent affinity chromatography runs were performed.

Results

It can be seen in FIG. 1 that an efficient CRP depletion from the blood has taken place during the reference measurement (i.e. without citrate). The percentage depletion at the beginning of the sample application to the column was over 90% (see FIG. 5 GV) and then declined to marginally below 50% in the further course of the sample application. Such a drop can be explained by the fact that the used column has bound more and more CRP with persistent sample application and is thus becoming more and more saturated.

Surprisingly, however, at a mixing ratio of 1:50 to 1:5 a CRP depletion corresponding to the depletion performance under reference conditions (see also FIG. 1) is found. Contrary to all expectations, an efficient CRP removal from blood plasma under the use according to the invention of a citrate solution for the affinity-chromatographic removal of CRP from biological fluids could be effected by means of a column material functionalized with ω-phosphonooxyalkyl ammonium groups and/or with ω-ammoniumalkoxy-hydroxy-phosphoryloxy groups.

Example 2: Hu-CRP ELISA for the Determination of the CRP Concentration in Samples In order to determine the effectiveness of an affinity-chromatographic purification of CRP from biological fluids e.g. blood plasma, the concentration of human CRP (hu-CRP) in the appropriate samples were determined by means of an immunoassay (ELISA, Enzyme Linked Immunosorbent Assay).

To this end, the wells of a microtiter plate were first coated with an antibody directed against human CRP by adding 100 µl of a solution of rabbit polyclonal anti-human CRP antibody (Dako, Hamburg, Germany, product number Q0329), diluted 1:500 in coating buffer (0.1 M NaHCO$_3$), incubated for 1 h at room temperature. It was then washed four times with at least 250 µl of PBST (0.1% Tween 20 in PBS).

For the determination of the concentration, sample buffer (5 mM EDTA in PBST) as a zero calibration and a standard series with concentrations of 300, 200, 100, 50, 30, 15 and 8.3 ng CRP/ml (in sample buffer) were used. For the standard series, a commercially available CRP standard (Human Serum C Reactive Protein Calibrator, 162 mg CRP/L, Dako, product number X0923) was diluted accordingly with sample buffer.

In addition, a reference sample with a high CRP concentration (Human Serum C Reactive Protein High Control, Dako, product number X0926) was diluted 1:600 and 1:1500 with sample buffer and a reference sample with a low CRP concentration (Human Serum C-Reactive Protein Low Control, Dako, product number X0925) diluted 1:250 and 1:1000 with sample buffer and used as additional reference samples for the ELISA. The actual samples to be measured (i.e. starting material, flow pool, flow fractions) were applied to the microtiter plate in three dilutions (in sample buffer).

For each well of the microtiter plate, 100 µl each were applied, incubated for 1.5 hours at room temperature and agitation on a shaker (600 revolutions per minute) and then washed four times with at least 250 µl of PBST.

For the detection, a peroxidase (POD)-labelled antibody (rabbit anti-huCRP-POD conjugate, 20 µg/ml stock solution, diluted 1:1000) and a competitive polyclonal anti-human CRP antibody from rabbits (Dako, Product number Q0329, diluted 1:2000) in blocking solution (1% casein, 0.9% NaCl, 0.001% thiomersal) were added subsequently. 100 µl per well were again applied, incubated for 1.5 h at room temperature and agitation on a shaker (600 revolutions per minute) and then washed again four times with at least 250 µl of PBST.

Subsequently, the substrate was added for the detection reaction. A solution of 3,3',5,5'-tetramethylbenzidine (TMB, 25 mg/ml in DMSO and EtOH) was diluted in substrate buffer (0.01% H$_2$O$_2$ in 0.2 M citric acid, pH 3.95) and 100 µl thereof was pipette into each well. After an incubation for 10 to 15 minutes in the dark, the detection reaction was stopped by the addition of 50 µl of stop solution per well. The photometric detection was then carried out by means of a microtiter plate reader (BioRad 680 XR, BioRad, Munich, Germany) by determining the extinction at 450 nm (reference 655 nm). A double determination of each microtiter plate was carried out in each case in order to eliminate measuring inaccuracies caused by the device. In addition, each experiment was repeated three times to increase the reproducibility of the results.

In preliminary experiments, an influence of the citrate concentrations used on the reliability of the hu-CRP-ELISA was excluded.

It should be pointed out here that, of course, other methods for the determination of CRP can also be used to determine the CRP concentration in the samples to be examined.

Example 3: CRP Depletion Under Citrate

Figure 2:
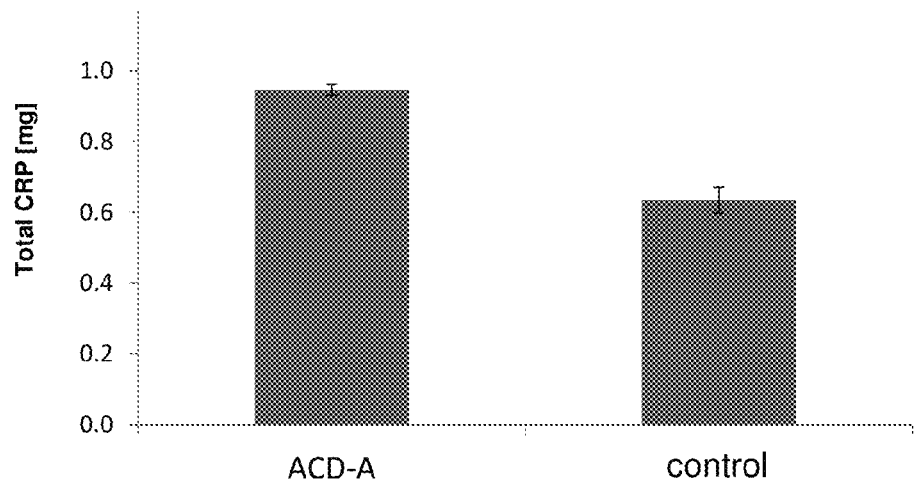
FIG. 2: The bar graph shows the depleted amount of CRP in blood plasma purified by affinity chromatography with and without the addition of citrate by means of a column material functionalized with ω-phosphonooxyalkyl ammonium groups and/or with ω-ammoniumalkoxy-hydroxyphosphoryloxy groups.

A blood plasma with a defined CRP concentration (38.8 mg/l) was divided into 12.5 ml each. One half was diluted with the addition of citrate (acid-citrate-dextrose-solution A (ACD-A)-solution 1:15) over the affinity chromatography column (0.5 ml matrix volume of agarose coupled with 4-aminophenylphosphocholine), the other half was passed without ACD-A over an identical column. The CRP content was determined before and after apheresis. From this, the distant amount of CRP was calculated. It was found that after addition of citrate, more CRP binds to the column and is removed. The results are shown in FIG. 2

Figure 3:
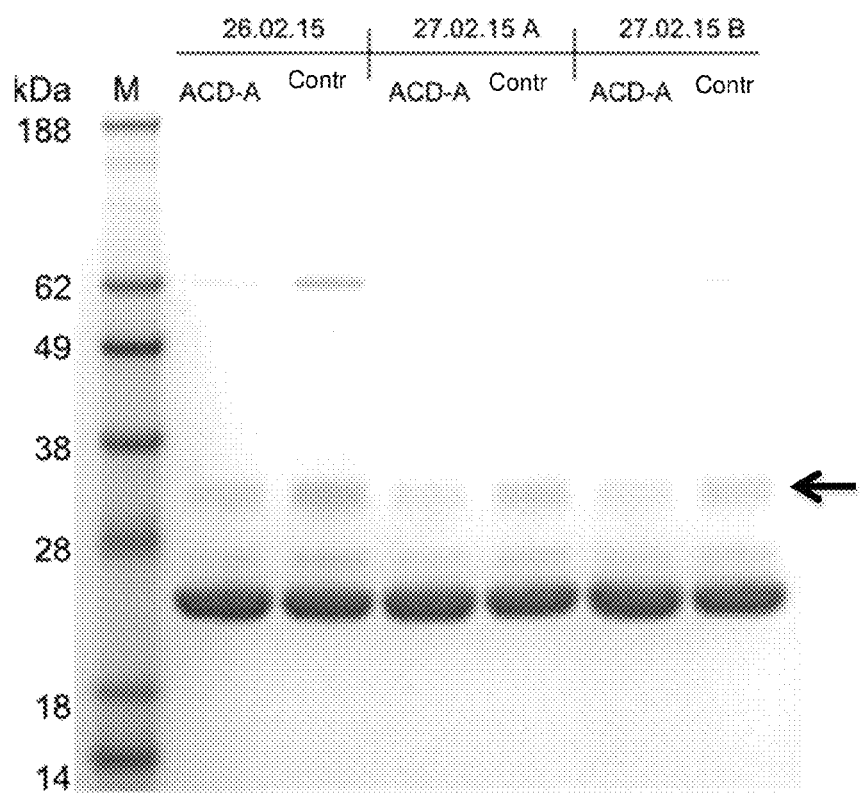
FIG. 3: shows an SDS gel applied to the blood plasma that was purified on three different days with and without the addition of citrate by means of a column material functionalized with ω-phosphonooxyalkyl ammonium groups and/or with ω-ammoniumalkoxy-hydroxy-phosphoryloxy groups, by affinity chromatography. The arrow marks the C1q band. This band contains less protein in the eluate from the blood plasma, which was mixed with ACD-A.

The eluates were also applied to an SDS gel, the photo of which is shown in FIG. 3. It is shown that in the apheresis with citrate (ACD-A) less complement (C1q) is removed than in apheresis without citrate solution.

The capacity increase of the column due to the citrate is explained by the present inventors, without claim to correctness, as follows. Complement binds to CRP bound to ω-phosphonooxyalkyl ammonium groups or ω-ammoniumalkoxy-hydroxy-phosphoryloxy groups. It seems that in the presence of citrate, less complement is activated and less of the C1q/C1r/C1s complexes bind. If the C1-4/C1r/C1s complexes bind directly or indirectly to the column material, less steric hindrance of the CRP bond also occurs due to these rather large complexes.

Overall, the addition of a citrate solution to the biological fluid to be purified leads to an increase in the capacity of the column material functionalized by means of ω-phosphonooxyalkyl ammonium groups and/or ω-ammoniumalkoxy-hydroxy-phosphoryloxy groups. Furthermore, less complement is activated. In a comparison with peptidic ligands, this increase in capacity was not observed by citrate.

The invention claimed is:

1. Use of a citrate solution for the affinity-chromatographic removal of the C-reactive protein (CRP) from biological fluids using a column material functionalized with a ω-phosphonooxyalkyl ammonium groups and/or with ω-ammoniumalkoxy-hydroxy-phosphoryloxy groups, wherein the citrate solution serves as a binding buffer for the affinity-chromatographic removal of CRP from biological fluids.

2. Use of a citrate solution according to claim 1, characterized in that the ω-phosphonooxyalkyl ammonium groups have the following general formula (I):

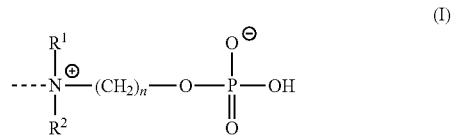

wherein
n is selected from 2 and 3;
$R^1$ and $R^2$ are independently selected from: —H, —CH$_3$, —C$_2$H$_5$, —C$_3$H$_7$, —C$_4$H$_9$, —C$_5$H$_{11}$, C$_6$H$_{13}$, or $R^1$ and $R^2$ together with the nitrogen atom to which they are attached can forms a heterocycle selected from:

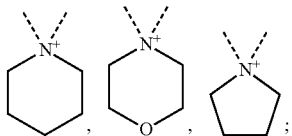

wherein one or more hydrogen atom(s) can be replaced by (a) fluorine atom(s).

3. Use of a citrate solution according to claim 1, characterized in that the ω-ammoniumalkoxy-hydroxy-phosphoryloxy groups have the following general formula (II):

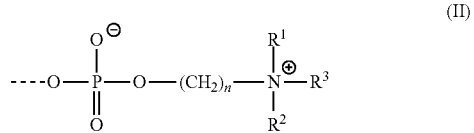

(II)

wherein
n is selected from 2 and 3;
$R^1$, $R^2$ and $R^3$ are independently selected from: —H, —CH$_3$, —C$_2$H$_5$, —C$_3$H$_7$, —C$_4$H$_9$, —C$_5$H$_{11}$, C$_6$H$_{13}$, or $R^1$ and $R^2$ together with the nitrogen atom to which they are attached can forms a heterocycle selected from:

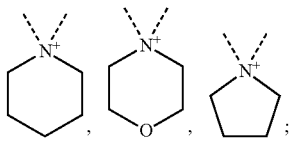

and
$R^3$ is selected from: H, —CH$_3$, —C$_2$H$_5$, —C$_3$H$_7$, —C$_4$H$_9$, —C$_5$H$_{11}$, C$_6$H$_{13}$, and preferably —H;
wherein one or more hydrogen atom(s) can be replaced by (a) fluorine atom(s).

4. Use of a citrate solution according to claim 1, wherein the citrate solution contains at least one of the citrate compounds from the group comprising or consisting of citric acid, sodium dihydrogen citrate, disodium hydrogen citrate, trisodium citrate, trisodium citrate dihydrate, potassium dihydrogen citrate, dipotassium hydrogen citrate, tripotassium citrate, lithium dihydrogen citrate, dilithium hydrogen citrate, trilithium citrate, ammonium dihydrogen citrate, diammonium hydrogen citrate, triammonium citrate, tricalcium dicitrate (calcium citrate), trimagnesium dicitrate (magnesium citrate) and/or partial citrate esters.

5. Use of a citrate solution according to claim 4, wherein the at least one citrate compound is selected from citric acid and citrate salts with monovalent metal cations.

6. Use of a citrate solution according to claim 4, wherein the citrate solution contains no additional Ca$^{2+}$ chelators apart from the citrate compound(s).

7. Use of a citrate solution according to claim 1, wherein the citrate solution comprises consisting of citric acid, trisodium citrate, D-glucose and water.

8. Use of a citrate solution according to claim 1, wherein the citrate solution has a total concentration of citrate in a range from 50 mM to 200 mM.

9. Use of a citrate solution according to claim 1, wherein the citrate solution has a pH-value in a range from pH 4.0 to pH 7.0.

10. Use of a citrate solution according to claim 1 in a dilution in a range from 1:50 to 1:5 with the biological fluid.

11. Use of a citrate solution according to claim 1, wherein the biological fluids are blood or blood plasma.

* * * * *